(12) United States Patent
Cahoon et al.

(10) Patent No.: US 6,184,036 B1
(45) Date of Patent: Feb. 6, 2001

(54) ORNITHINE BIOSYNTHESIS ENZYMES

(75) Inventors: Rebecca E. Cahoon; J. Antoni Rafalski, both of Wilmington; Saverio Carl Falco, Arden, all of DE (US)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/347,819

(22) Filed: Jul. 2, 1999

Related U.S. Application Data

(60) Provisional application No. 60/093,209, filed on Jul. 17, 1998.

(51) Int. Cl.[7] ............................ A01H 1/00; C07H 21/02; C07H 21/04; C07K 14/415; C12N 5/10
(52) U.S. Cl. ............................ 435/419; 435/6; 435/183; 435/193; 435/410; 435/419; 435/252.3; 435/320.1; 530/350; 530/370; 536/23.1; 536/23.6; 536/24.1; 800/278
(58) Field of Search .................... 435/6, 183, 193, 435/410, 419, 252.3, 320.1; 530/350, 370; 536/23.1, 23.6, 24.1; 800/278

(56) References Cited

U.S. PATENT DOCUMENTS 5,356,796 * 10/1994 Keller .

OTHER PUBLICATIONS

Inana et al. PNAS USA., vol. 83, Mar. 1986, p. 1203–1207.*
NCBI General Identifier No. 2492863.
NCBI General Identifier No. 1749516.
DNA Res. 496), pp. 363–369 (1997).
NCBI General Identifier No. 5055676.
NCBI General Identifier No. 1709425.
NCBI General Identifier No. 5003938.

* cited by examiner

Primary Examiner—Phuong T. Bui

(57) ABSTRACT

This invention relates to an isolated nucleic acid fragment encoding an ornithine-oxo-acid transaminase. The invention also relates to the construction of a chimeric gene encoding all or a portion of the ornithine-oxo-acid transaminase, in sense or antisense orientation, wherein expression of the chimeric gene results in production of altered levels of the ornithine-oxo-acid transaminase in a transformed host cell.

7 Claims, No Drawings

US 6,184,036 B1

ORNITHINE BIOSYNTHESIS ENZYMES

This application claims priority benefit of U.S. Provisional application Ser. No. 60/093,209 filed Jul. 17, 1998.

FIELD OF THE INVENTION

This invention is in the field of plant molecular biology. More specifically, this invention pertains to nucleic acid fragments encoding ornithine biosynthetic enzymes in plants and seeds.

BACKGROUND OF THE INVENTION

Ornithine is converted into arginine in the urea cycle. Intermediaries in the ornithine biosynthesis pathway are important in other steps of this cycle. Amino acid N-acetyl transferase (EC 2.3.1.1) catalyzes the first reaction in a pathway that leads to the synthesis of ornithine from L-glutamate giving N-acetylglutamate as its intermediary product. Amino acid N-acetyl transferase is also known as N-acetylglutamate synthetase (AGS) and is encoded by the argA locus in bacteria. No plant N-acetylglutamate has been described to date.

Carbamoyl phosphate synthase I, the mitochondrial enzyme that catalyzes the first committed step of the urea cycle, is allosterically activated by N-acetyl glutamate. The rate of urea production by the liver is, in fact, correlated with the N-acetylglutamate concentration. Increased urea synthesis is required when amino acid breakdown rates increase, generating excess nitrogen that must be extracted. Increase in these breakdown rates are signaled by an increase in glutamate concentration through transamination reaction. This situation, in turn, causes an increase in N-acetylglutamate synthesis, stimulating carbamoyl phosphate synthetase and the entire urea cycle.

Ornithine oxo-acid transaminase (EC 2.6.1.13), also called omithine aminotransferase, catalyzes the conversion of omithine to L-glutamate semialdehyde. The gene encoding ornithine oxo-acid transaminase has been cloned from *Aspergillus nidulans, Saccharomyces cerevisiae, Plasmodium falciparum, Vigna aconitifolia*, rat, mouse and man. No plant sequences encoding omithine oxo-acid transaminase have been described to date.

SUMMARY OF THE INVENTION

The instant invention relates to isolated nucleic acid fragments encoding ornithine-oxo-acid transaminase. Specifically, this invention concerns an isolated nucleic acid fragment encoding an ornithine-oxo-acid transaminase and an isolated nucleic acid fragment that is substantially similar to an isolated nucleic acid fragment encoding an omithine-oxo-acid transaminase. In addition, this invention relates to a nucleic acid fragment that is complementary to the nucleic acid fragment encoding omithine-oxo-acid transaminase.

An additional embodiment of the instant invention pertains to a polypeptide encoding all or a substantial portion of an omithine-oxo-acid transaminase.

In another embodiment, the instant invention relates to a chimeric gene encoding an ornithine-oxo-acid transaminase, or to a chimeric gene that comprises a nucleic acid fragment that is complementary to a nucleic acid fragment encoding an ornithine-oxo-acid transaminase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an ornithine-oxo-acid transaminase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an ornithine-oxo-acid transaminase in a transformed host cell comprising: a) transforming a host cell with a chimeric gene comprising a nucleic acid fragment encoding an ornithine-oxo-acid transaminase; and b) growing the transformed host cell under conditions that are suitable for expression of the chimeric gene wherein expression of the chimeric gene results in production of altered levels of ornithine-oxo-acid transaminase in the transformed host cell.

An addition embodiment of the instant invention concerns a method for obtaining a nucleic acid fragment encoding all or a substantial portion of an amino acid sequence encoding an ornithine-oxo-acid transaminase.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptide, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Ornithine-Oxo-Acid Transaminase

| Plant | Clone Designation | SEQ ID NO: (Nucleotide) | (Amino Acid) |
|---|---|---|---|
| Corn | Contig of:<br>cen3n.pk0204.g9<br>p0015.cdped57r<br>p0128.cpibt92r | 1 | 2 |
| Rice | r10n.pk119.k7 | 3 | 4 |
| Rice | Contig of:<br>rds1c.pk002.m1<br>r10n.pk0003.b1<br>rlr2.pk0015.a2<br>rlr2.pk0033.f4 | 5 | 6 |
| Soybean | sgs4c.pk005.o1 | 7 | 8 |
| Wheat | Contig of:<br>wlk1.pk0024.b2<br>wre1n.pk0004.b7 | 9 | 10 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6X SSC, 0.5% SDS at room temperature for 15 min, then repeated with 2X SSC, 0.5% SDS at 45° C. for 30 min, and then repeated twice with 0.2X SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased to 60° C. Another preferred set of highly stringent conditions uses two final washes in 0.1X SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol*. 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several ornithine-oxo-acid transaminases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other ornithine-oxo-acid transaminases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptide are present at higher or lower levels than normal or in cell types or developmental stages in which they are not normally found. This would have the effect of altering the level of arginine in those cells. Extra arginine resulting from an increase in ornithine biosynthesis may have nutraceutical utility. Manipulation of the levels of ornithine-oxo-acid transaminase may result in plants which are more resistant to salt stress.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptide to different cellular compartments, or to facilitate its secretion from the cell. It is thus envisioned that the chimeric gene described above may be further supplemented by altering the coding sequence to encode the instant polypeptide with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptide in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptide (or portions thereof) may be produced in heterologous host cells, particularly in the cells of microbial hosts, and can be used to prepare antibodies to the these proteins by methods well known to those skilled in the art. The antibodies are useful for detecting the polypeptide of the instant invention in situ in cells or in vitro in cell extracts. Preferred heterologous host cells for production of the instant polypeptide are microbial hosts. Microbial expression systems and expression vectors containing regulatory sequences that direct high level expression of foreign proteins are well known to those skilled in the art. Any of these could be used to construct a chimeric gene for production of the instant polypeptide. This chimeric gene could then be introduced into appropriate microorganisms via transformation to provide high level expression of the encoded ornithine-oxo-acid transaminase. An example of a vector for high level expression of the instant polypeptide in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rick, Soybean and Wheat

| Library | Tissue | Clone |
|---------|--------|-------|
| cen3n | Corn Endosperm 20 Days After Pollination* | cen3n.pk0204.g9 |
| p0015 | Corn Embryo 13 Days After Pollination | p0015.cdped57r |
| p0128 | Corn Primary and Secondary Immature Ear | p0128.cpibt92r |
| rds1c | Rice Developing Seeds | rds1c.pk002.m1 |
| rl0n | Rice 15 Day Old Leaf* | rl0n.pk119.k7 |
|       |                        | rl0n.pk0003.b1 |
| rlr2 | Rice Leaf 15 Days After Germination, 2 Hours After Infection of Strain *Magaporthe grisea* 4360-R-62 (AVR2-YAMO); Resistant | rlr2.pk0015.a2 rlr2.pk0033.f4 |
| sgs4c | Soybean Seeds 2 Days After Germination | sgs4c.pk005.o1 |
| wlk1 | Wheat Seedlings 1 Hour After Treatment With Herbicide** | wlk1.pk0024.b2 |
| wre1n | Wheat Root From 7 Day Old Etiolated Seedling* | wre1n.pk0004.b7 |

*These libraries were normalized essentially as described in U.S. Pat. No. 5,482,845, incorporated herein by reference.
**Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding ornithine-oxo-acid transaminase were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding

Ornithine-Oxo-Acid Transaminase

The BLASTX search using the EST sequences from clones listed in Table 3 revealed similarity of the polypeptides encoded by the cDNAs to ornithine-oxo-acid transaminase from *Emericella nidulans* (NCBI General Identifier No. 2492863), *Schizosaccharomyces pombe* (NCBI General Identifier No. 1749516), or *Drosophila ananassae* (NCBI General Identifier No. 1709425). Shown in Table 3 are the organism with similarity, the NCBI General Identifier and the BLAST results for individual ESTs ("EST"), the sequences of the entire CDNA inserts comprising the indicated cDNA clones ("FIS"), or contigs assembled from two or more ESTs ("Contig"):

TABLE 3

BLAST Results for Sequences Encoding Polypeptides Homologous to Ornithine-Oxo-Acid Transaminase

| Clone | Status | Organism | GI | BLAST pLog Score |
|---|---|---|---|---|
| Contig of: cen3n.pk0204.g9 p0015.cdped57r p0128.cpibt92r | FIS | *Emericella nidulans* | 2492863 | 124.00 |

TABLE 3-continued

BLAST Results for Sequences Encoding Polypeptides Homologous to Ornithine-Oxo-Acid Transaminase

| Clone | Status | Organism | GI | BLAST pLog Score |
|---|---|---|---|---|
| rl0n.pk119.k7 | EST | *Emericella nidulans* | 2492863 | 16.00 |
| Contig of: rds1c.pk002.m1 rl0n.pk0003.b1 rlr2.pk0033.f4 | FIS | *Schizosaccharomyces pombe* | 1749516 | 92.70 |
| sgs4c.pk005.o1 | EST | *Drosphila ananassae* | 1709425 | 47.00 |
| Contig of: wlk1.pk0024.b2 wre1n.pk0004.b7 | Contig | *Emericella nidulans* | 2492863 | 77.52 |

The 5' end of the sequence in p0128.cpibt92r was obtained by RACE PCR using primers:
5'-CGA TGA ATA CTG GTG CTG AAG G-3' (SEQ ID NO:11)
5'-CAC AAA TCC GAT CTC CAA GCT C-3' (SEQ ID NO:12)
5'-ACC CCA GCT TCA CCT TGG ATA G-3' (SEQ ID NO:13)
5'-TGG ATC TCA TCA GCA ATC ATC AA-3' (SEQ ID NO:14)

The primers were used in a standard PCR reaction (heat at 94° for 1 min, followed by 35 cycles of 94° for 30 sec, 63° for 30 sec and 72° for 4 min, followed with 72° for 7 min and holding at 15°) using DNA from the crl library as the template DNA.

Nucleotides 1354 to 1840 of the sequence from the contig assembled of clones cen3n.pk0204.g9, p0015.cdped57r and p0128.cpibt92r are 100% identical to nucleotides 584 to 98 of a 594 nucleotide corn EST (NCBI General Identifier No. 5055676). Nucleotides 10 through 222 from the sequence of the contig assembled of clones rds1c.pk002.m1, rl0n.pk0003.b1, rlr2.pk0015.a2 and rlr2.pk0033.f4 are 92% identical to nucleotides 3 through 213 of a 216 nt rice EST (NCBI General Identifier No. 5003938).

BLAST scores and probabilities indicate that the nucleic acid fragments comprising the instant cDNA clones encode an entire corn ornithine-oxo-acid transaminase, a substantial portion of a rice ornithine-oxo-acid transaminase and portions of rice, soybean and wheat ornithine-oxo-acid transaminase. These sequences represent the first plant sequences encoding ornithine-oxo-acid transaminase.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptide in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptide can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated nucleic acid fragment comprising a member selected from the group consisting of:
   (a) an isolated nucleic acid fragment encoding an orthinine-oxo-acid transaminase that is at least 500 contiguous nucleotides that hybridizes under highly stringent conditions to an isolated nucleic acid fragment encoding the amino acid sequence set forth in SEQ ID NO:2, wherein said highly stringent conditions is defined by washes with 6× SSC, 0.5% SDS at room temperature for 15 min, then repeated with 2× SSC, 0.5% SDS at 45° C. for 30 min, and two washes in 0.1× SSC, 0.1% SDS at 65° C.;
   (b) an isolated nucleic acid fragment encoding an orthinine-oxo-acid transaminase that is at least 250 nucleotides that hybridizes under highly stringent conditions to an isolated nucleic acid fragment encoding the amino acid sequence set forth in a member selected from the group consisting of SEQ ID NO:4, SEQ ID NO:6, SEQ ID NO:8, and SEQ ID NO:10, wherein said highly stringent conditions is defined in (a); and
   (c) an isolated nucleic acid fragment that is fully complementary to the nucleic acid fragment of (a) or (b).

2. The isolated nucleic acid fragment of claim 1 wherein the nucleotide sequence of the fragment comprises the sequence set forth in a member selected from the group consisting of SEQ ID NO:1, SEQ ID NO:3, SEQ ID NO:5, SEQ ID NO:7 and SEQ ID NO:9.

3. The nucleic acid fragment of claim 1 operably linked to at least one regulatory sequence.

4. A transformed cell comprising the nucleic acid fragment of claim 3.

5. An isolated nucleic acid fragment comprising a member selected from the group consisting of:
   (a) an isolated nucleic acid fragment encoding an orthinine-oxo-acid transaminase that is at least 500 contiguous nucleotides that hybridizes under highly stringent conditions to an isolated nucleic acid fragment having a nucleotide sequence set forth in SEQ ID NO:1, wherein said highly stringent conditions is defined by washes with 6× SSC, 0.5% SDS at room temperature for 15 min, then repeated with 2× SSC, 0.5% SDS at 45° C. for 30 min, and two washes in 0.1× SSC, 0.1% SDS at 65° C.;
   (b) an isolated nucleic acid fragment encoding an orthinine-oxo-acid transaminase that is at least 250 nucleotides that hybridizes under highly stringent conditions to an isolated nucleic acid fragment having a nucleic acid sequence set forth in a member selected from the group consisting of SEQ ID NO:3, SEQ ID NO:5, SEQ ID NO:7, and SEQ ID NO:9, wherein said highly stringent conditions is defined in (a); and
   (c) an isolated nucleic acid fragment that is fully complementary to the nucleic acid fragment of (a) or (b).

6. The isolated nucleic acid fragment of claim 1 wherein said nucleic acid is RNA.

7. The isolated nucleic acid fragment of claim 5 wherein said nucleic acid is RNA.

\* \* \* \* \*

SEQUENCE LISTING

<160> NUMBER OF SEQ ID NOS: 14

<210> SEQ ID NO 1
<211> LENGTH: 1858
<212> TYPE: DNA
<213> ORGANISM: Zea mays
<220> FEATURE:
<221> NAME/KEY: unsure
<222> LOCATION: (10)
<220> FEATURE:
<221> NAME/KEY: unsure
<222> LOCATION: (1138)
<220> FEATURE:
<221> NAME/KEY: unsure
<222> LOCATION: (1175)
<220> FEATURE:
<221> NAME/KEY: unsure
<222> LOCATION: (1201)
<220> FEATURE:
<221> NAME/KEY: unsure
<222> LOCATION: (1342)
<220> FEATURE:
<221> NAME/KEY: unsure
<222> LOCATION: (1344)

<400> SEQUENCE: 1

```
cctttaattn ccctttgcag gaatccggca cgaggcccgc cggctcggac ccggaggctg     60
cagcggcacc gggatctggg aatctacacg gcctggagcc tccagcgact ggccccacca    120
ccatttgcgc gcgcgcgcga gggaccggcc ggcgaacaga ggcgccactg agctctgagc    180
gggtgcggcc gggcatggcg acggcgctgg cgcggcgggg cgccgcggcc ctggcgcggt    240
ggcgcgggat gtgctcgagc tcggcgtcgg cgccgcggag cgccgcggcg ctgtcctcag    300
aggagctcat gcggatggaa caagactgca gcgcgcataa ttaccatcca atccccatgg    360
tgttttccaa aggagaaggt tcacacatag tggaccccga aggcaacaaa tacattgatt    420
ttctctctgc ttattctgca gtcaatcagg gtcattgcca tccaaaagtc ctgagagctt    480
tgatagaaca ggcagaaagt cttacgctca gttctagagc tttctacaat gataagttcc    540
caatctttgc ggaatatctg acaagcatgt ttggatatga catgatgttg ccgatgaata    600
ctggtgctga aggagttgaa actgctatca agctggctag gaaatggggt tatgagaaga    660
aacatatacc aaagaatgag gctttgcttg tctcttgctg tgggtgtttc catggtcgaa    720
ctcttggtgt catttccatg agctgtgaca acgatgcaac tcgtggtttt ggtccttttgg    780
ttcctggcca tcttaaagtt gattttggag atattgatgg gttaaagaaa atcttcgaag    840
agcttggaga tcggatttgt ggttttttat ttgaacctat ccaaggtgaa gctggggtag    900
taatcccacc agatggctat ttgaaaggtg ccagagactt gtgttctaaa cacaacgttt    960
tgatgattgc tgatgagatc caaactggca tagctagaac tggtaaaatg ctggcatgtg   1020
actgggaaaa catacggcct gacatggtga ttctaggcaa agcactcggt gctggagttg   1080
ttccagtcag tgcagttctt gcagacaagg atgtcatgct gtgtatcaga ccaggggnga   1140
acatgggaag tacattcggt ggggaatccg ttaanctagc gctgtggcca ttgccatcac   1200
ntgaaaatgg gtccagagac gaaggtcttg ttgaaagggc tgcaaagtta ggacaggagt   1260
ttagggacca gttacagaag gtccagcaga aattccctca atcctaaga gaagtgcgcg   1320
ggagggtttt gctgaacgca gngnatctaa acaacgacgc gctatctcct gcttctgcat   1380
atgacatctg catcaagttg aaggagagag gcattttagc gaaacccaca catgacacta   1440
taatccgact tgctcctccc ctcacaatca gtcctgagga gcttgcagaa gcatccaagg   1500
```

```
cgcttagtga cgtgctggag catgacttgc cacagctgca gctgcagaag cagataaaaa   1560
agccagaatc tgaggcagag aagccagtct gtgacagatg cggccgggac ttgtacggat   1620
gaatgaagcc tccgaacaga gataacttca ttttcgtagg cacccatctc gccccagaag   1680
aaataataac agagcagagg atgccagctg cctagctact tgggttaccg taatgttatg   1740
cgacttgttg catcgtatac caagtatatg agctattgca accttggtga atatgtcaaa   1800
taaatggcag cattcacatg ctcaaatatg ggcagcattc aaaaaaaaaa aaaaaaaa    1858
```

<210> SEQ ID NO 2
<211> LENGTH: 533
<212> TYPE: PRT
<213> ORGANISM: Zea mays
<220> FEATURE:
<221> NAME/KEY: UNSURE
<222> LOCATION: (315)
<220> FEATURE:
<221> NAME/KEY: UNSURE
<222> LOCATION: (327)
<220> FEATURE:
<221> NAME/KEY: UNSURE
<222> LOCATION: (336)
<220> FEATURE:
<221> NAME/KEY: UNSURE
<222> LOCATION: (383)..(384)

<400> SEQUENCE: 2

```
Met Ala Thr Ala Leu Ala Arg Arg Gly Ala Ala Leu Ala Arg Trp
 1               5                  10                  15

Arg Gly Met Cys Ser Ser Ala Ser Ala Pro Arg Ser Ala Ala Ala
                20                  25                  30

Leu Ser Ser Glu Glu Leu Met Arg Met Glu Gln Asp Cys Ser Ala His
            35                  40                  45

Asn Tyr His Pro Ile Pro Met Val Phe Ser Lys Gly Glu Gly Ser His
        50                  55                  60

Ile Val Asp Pro Glu Gly Asn Lys Tyr Ile Asp Phe Leu Ser Ala Tyr
 65                  70                  75                  80

Ser Ala Val Asn Gln Gly His Cys His Pro Lys Val Leu Arg Ala Leu
                85                  90                  95

Ile Glu Gln Ala Glu Ser Leu Thr Leu Ser Ser Arg Ala Phe Tyr Asn
            100                 105                 110

Asp Lys Phe Pro Ile Phe Ala Glu Tyr Leu Thr Ser Met Phe Gly Tyr
        115                 120                 125

Asp Met Met Leu Pro Met Asn Thr Gly Ala Glu Gly Val Glu Thr Ala
    130                 135                 140

Ile Lys Leu Ala Arg Lys Trp Gly Tyr Glu Lys Lys His Ile Pro Lys
145                 150                 155                 160

Asn Glu Ala Leu Leu Val Ser Cys Cys Gly Cys Phe His Gly Arg Thr
                165                 170                 175

Leu Gly Val Ile Ser Met Ser Cys Asp Asn Asp Ala Thr Arg Gly Phe
            180                 185                 190

Gly Pro Leu Val Pro Gly His Leu Lys Val Asp Phe Gly Asp Ile Asp
        195                 200                 205

Gly Leu Lys Lys Ile Phe Glu Glu Leu Gly Asp Arg Ile Cys Gly Phe
    210                 215                 220

Leu Phe Glu Pro Ile Gln Gly Glu Ala Gly Val Val Ile Pro Pro Asp
225                 230                 235                 240

Gly Tyr Leu Lys Gly Ala Arg Asp Leu Cys Ser Lys His Asn Val Leu
```

```
                          245                 250                 255
Met Ile Ala Asp Glu Ile Gln Thr Gly Ile Ala Arg Thr Gly Lys Met
                260                 265                 270
Leu Ala Cys Asp Trp Glu Asn Ile Arg Pro Asp Met Val Ile Leu Gly
            275                 280                 285
Lys Ala Leu Gly Ala Gly Val Val Pro Val Ser Ala Val Leu Ala Asp
        290                 295                 300
Lys Asp Val Met Leu Cys Ile Arg Pro Gly Xaa Asn Met Gly Ser Thr
305                 310                 315                 320
Phe Gly Gly Glu Ser Val Xaa Leu Ala Leu Trp Pro Leu Pro Ser Xaa
                325                 330                 335
Glu Asn Gly Ser Arg Asp Glu Gly Leu Val Glu Arg Ala Ala Lys Leu
                340                 345                 350
Gly Gln Glu Phe Arg Asp Gln Leu Gln Lys Val Gln Gln Lys Phe Pro
            355                 360                 365
Gln Ile Leu Arg Glu Val Arg Gly Arg Gly Leu Leu Asn Ala Xaa Xaa
        370                 375                 380
Leu Asn Asn Asp Ala Leu Ser Pro Ala Ser Ala Tyr Asp Ile Cys Ile
385                 390                 395                 400
Lys Leu Lys Glu Arg Gly Ile Leu Ala Lys Pro Thr His Asp Thr Ile
                405                 410                 415
Ile Arg Leu Ala Pro Pro Leu Thr Ile Ser Pro Glu Glu Leu Ala Glu
                420                 425                 430
Ala Ser Lys Ala Leu Ser Asp Val Leu Glu His Asp Leu Pro Gln Leu
            435                 440                 445
Gln Leu Gln Lys Gln Ile Lys Lys Pro Glu Ser Glu Ala Glu Lys Pro
        450                 455                 460
Val Cys Asp Arg Cys Gly Arg Asp Leu Tyr Gly Gln Leu Gln Leu Gln
465                 470                 475                 480
Lys Gln Ile Lys Lys Pro Glu Ser Glu Ala Glu Lys Pro Val Cys Asp
                485                 490                 495
Arg Cys Gly Arg Asp Leu Tyr Gly Gln Leu Gln Leu Gln Lys Gln Ile
                500                 505                 510
Lys Lys Pro Glu Ser Glu Ala Glu Lys Pro Val Cys Asp Arg Cys Gly
            515                 520                 525
Arg Asp Leu Tyr Gly
        530

<210> SEQ ID NO 3
<211> LENGTH: 584
<212> TYPE: DNA
<213> ORGANISM: Oryza sativa

<400> SEQUENCE: 3
cagctacaga aggttcaaca gagattcccg caaatcataa gggaagtacg tgggagggt      60 ttgcttaatg cagtggatct aagcaacgaa gctttatccc ctgcttctgc ttacgacatc    120
tgcatcaagc tgaaggagag aggcgttctg caaagcccac acatgacac cataatcaga     180 ttagcgcctc cgctgtcaat cagtcctgag gagcttgcag aagcatcgaa ggcgttcagc    240
gatgtgcttg agcatgacct gccacagctg cagaagcaga tcaagaagac agaatccgcg    300
gcagaaaaac aatcctgtga cagatgcggc agagacttgt actgatgagt gatagacgag    360
acaatgaaac gtttccagag gcacccgttt cgcccaaata aaatagcaga acacacctcg    420
cgaattcata gctcattgta gtagtagagt aggatatata cacctccttg ttgcgatgtc    480
```

```
tgggacatat ggtccaggga tttgtcgcct aatcgagctg gttgcaaaca aatggggtag      540
cattattcta gtctatcata tcatgcaaaa aaaaaaaaaa aaaa                      584
```

<210> SEQ ID NO 4
<211> LENGTH: 114
<212> TYPE: PRT
<213> ORGANISM: Oryza sativa

<400> SEQUENCE: 4

```
Gln Leu Gln Lys Val Gln Gln Arg Phe Pro Gln Ile Ile Arg Glu Val
  1               5                  10                  15

Arg Gly Arg Gly Leu Leu Asn Ala Val Asp Leu Ser Asn Glu Ala Leu
             20                  25                  30

Ser Pro Ala Ser Ala Tyr Asp Ile Cys Ile Lys Leu Lys Glu Arg Gly
         35                  40                  45

Val Leu Ala Lys Pro Thr His Asp Thr Ile Ile Arg Leu Ala Pro Pro
 50                  55                  60

Leu Ser Ile Ser Pro Glu Glu Leu Ala Glu Ala Ser Lys Ala Phe Ser
 65                  70                  75                  80

Asp Val Leu Glu His Asp Leu Pro Gln Leu Gln Lys Gln Ile Lys Lys
                 85                  90                  95

Thr Glu Ser Ala Ala Glu Lys Gln Ser Cys Asp Arg Cys Gly Arg Asp
            100                 105                 110

Leu Tyr
```

<210> SEQ ID NO 5
<211> LENGTH: 1117
<212> TYPE: DNA
<213> ORGANISM: Oryza sativa
<220> FEATURE:
<221> NAME/KEY: unsure
<222> LOCATION: (225)
<220> FEATURE:
<221> NAME/KEY: unsure
<222> LOCATION: (227)
<220> FEATURE:
<221> NAME/KEY: unsure
<222> LOCATION: (229)
<220> FEATURE:
<221> NAME/KEY: unsure
<222> LOCATION: (246)
<220> FEATURE:
<221> NAME/KEY: unsure
<222> LOCATION: (255)
<220> FEATURE:
<221> NAME/KEY: unsure
<222> LOCATION: (308)
<220> FEATURE:
<221> NAME/KEY: unsure
<222> LOCATION: (320)
<220> FEATURE:
<221> NAME/KEY: unsure
<222> LOCATION: (1043)
<220> FEATURE:
<221> NAME/KEY: unsure
<222> LOCATION: (1068)
<220> FEATURE:
<221> NAME/KEY: unsure
<222> LOCATION: (1070)
<220> FEATURE:
<221> NAME/KEY: unsure
<222> LOCATION: (1084)
<220> FEATURE:
<221> NAME/KEY: unsure
<222> LOCATION: (1100)
<220> FEATURE:
<221> NAME/KEY: unsure
<222> LOCATION: (1114)
<220> FEATURE:
<221> NAME/KEY: unsure
<222> LOCATION: (1116)

<400> SEQUENCE: 5

```
atcactccgt tgcgaaattt ttgcgagctc gcgacgcgaa ccccctacgc cgcagccgca      60
ggcttcctct tcatctcctc ctcctccaga cctccacgcg agcgtgcccc ggggtggaag     120
cggaggcggc ggcgggtcga gcgcaatctg gtggcgtggg ggcgcgtcac gatggcggcg     180
gcgctggcga cgcgtggcgg tgggggctg gcgcgcgccc tgacncngng gagggggatg      240
tgctcngcca cggcngccgt acgcgccgcc ggggcggcgc tgacgtccga tgagctcatg     300
ccgatggngc gcgagcgcan cgcgcacaac taccatccaa ttccggtggt gttctccaag     360
ggagaaggtt cacatatatt ggatcctgaa ggcaacaaat acattgattt cctgtctgct     420
tattctgcag tcaatcaggg ccattgccat ccaaaagtcc tgagagcgtt gaagagcag      480
gcagaaaggc tcacactgag ttctagagct ttctacaatg acaaattccc aatctttgca     540
gaatacctga caagcatgtt tgggtatgaa atgatgttgc cgatgaatac tggagctgaa     600
ggagtggaaa cagctatcaa attggtgagg aaatggggtt atgagaagaa aaagatacca     660
aaaaatgagg cttttgattgt ctcttgctgt ggatgttttc atggtcggac attaggtgtc     720
atctctatga gttgtgataa tgatgcaact cgtggttttg gcccattggt tcctggccat     780
cttaaagttg attttggaga cactgatggg ttggagaaaa tctttaaaga tcatggcgag     840
aggatatgtg gttttttgtt tgaaccaatc caaggagaag ctggggtaat aatcccacca     900
gatggctatt tgaaagctgt cagagatttg tgttcaaggc acaacattct gatgattgca     960
gatgagatcc aaacaggcat agctagaact gcaaatgctg gctgcgattg gggaaaacat    1020
acgacctgat gtggtgattc tanggcaagg ccttggtgct ggaatagntn ctgtaagtgc    1080
gggntctttg cagataaggn tattatgccg tggnanc                             1117
```

<210> SEQ ID NO 6
<211> LENGTH: 303
<212> TYPE: PRT
<213> ORGANISM: Oryza sativa
<220> FEATURE:
<221> NAME/KEY: UNSURE
<222> LOCATION: (19)..(20)
<220> FEATURE:
<221> NAME/KEY: UNSURE
<222> LOCATION: (46)
<220> FEATURE:
<221> NAME/KEY: UNSURE
<222> LOCATION: (50)
<220> FEATURE:
<221> NAME/KEY: UNSURE
<222> LOCATION: (291)
<220> FEATURE:
<221> NAME/KEY: UNSURE
<222> LOCATION: (299)..(300)

<400> SEQUENCE: 6

```
Met Ala Ala Ala Leu Ala Thr Arg Gly Gly Gly Leu Ala Arg Ala
 1               5                  10                  15

Leu Thr Xaa Xaa Arg Gly Met Cys Ser Ala Thr Ala Val Arg Ala
                20                  25                  30

Ala Gly Ala Ala Leu Thr Ser Asp Glu Leu Met Pro Met Xaa Arg Glu
            35                  40                  45

Arg Xaa Ala His Asn Tyr His Pro Ile Pro Val Val Phe Ser Lys Gly
    50                  55                  60
```

Glu Gly Ser His Ile Leu Asp Pro Glu Gly Asn Lys Tyr Ile Asp Phe
65                  70                  75                  80

Leu Ser Ala Tyr Ser Ala Val Asn Gln Gly His Cys His Pro Lys Val
            85                  90                  95

Leu Arg Ala Leu Lys Glu Gln Ala Glu Arg Leu Thr Leu Ser Ser Arg
            100                 105                 110

Ala Phe Tyr Asn Asp Lys Phe Pro Ile Phe Ala Glu Tyr Leu Thr Ser
        115                 120                 125

Met Phe Gly Tyr Glu Met Met Leu Pro Met Asn Thr Gly Ala Glu Gly
    130                 135                 140

Val Glu Thr Ala Ile Lys Leu Val Arg Lys Trp Gly Tyr Glu Lys Lys
145                 150                 155                 160

Lys Ile Pro Lys Asn Glu Ala Leu Ile Val Ser Cys Cys Gly Cys Phe
                165                 170                 175

His Gly Arg Thr Leu Gly Val Ile Ser Met Ser Cys Asp Asn Asp Ala
            180                 185                 190

Thr Arg Gly Phe Gly Pro Leu Val Pro Gly His Leu Lys Val Asp Phe
        195                 200                 205

Gly Asp Thr Asp Gly Leu Glu Lys Ile Phe Lys Asp His Gly Glu Arg
    210                 215                 220

Ile Cys Gly Phe Leu Phe Glu Pro Ile Gln Gly Glu Ala Gly Val Ile
225                 230                 235                 240

Ile Pro Pro Asp Gly Tyr Leu Lys Ala Val Arg Asp Leu Cys Ser Arg
                245                 250                 255

His Asn Ile Leu Met Ile Ala Asp Glu Ile Gln Thr Gly Ile Ala Arg
            260                 265                 270

Thr Ala Met Leu Ala Ala Ile Gly Glu Asn Ile Arg Pro Asp Val Val
        275                 280                 285

Ile Leu Xaa Gln Gly Leu Gly Ala Gly Ile Xaa Xaa Val Ser Ala
    290                 295                 300

<210> SEQ ID NO 7
<211> LENGTH: 536
<212> TYPE: DNA
<213> ORGANISM: Glycine max
<220> FEATURE:
<221> NAME/KEY: unsure
<222> LOCATION: (328)
<220> FEATURE:
<221> NAME/KEY: unsure
<222> LOCATION: (438)
<220> FEATURE:
<221> NAME/KEY: unsure
<222> LOCATION: (471)..(472)
<220> FEATURE:
<221> NAME/KEY: unsure
<222> LOCATION: (492)
<220> FEATURE:
<221> NAME/KEY: unsure
<222> LOCATION: (500)
<220> FEATURE:
<221> NAME/KEY: unsure
<222> LOCATION: (510)
<220> FEATURE:
<221> NAME/KEY: unsure
<222> LOCATION: (525)
<220> FEATURE:
<221> NAME/KEY: unsure
<222> LOCATION: (535)

<400> SEQUENCE: 7
gatatttcct ccagatggtt atttaaaagc tgttagagat ctttgctcca aatataatgt     60

```
cttgatgatt gctgatgaaa ttcaaactgg gttagcaaga acggggaaga tgctggcttg    120
tgagtgggaa gaagttcgcc cagatgttct gatactaggg aaagcattgg gtggaggagt    180
tataccagtt agtgcagttc ttgcagacaa agatgtgatg ctttgtatac aacctggaca    240
gcatggaagt acctttggtg gaaatccaat ggccagtgca gttgcaattg cctctctaga    300
agtaataaaa aatgagagac tcgttganag atctgcccaa atgggagagg agcttactgg    360
tcagctgctt aagattcagc agcaataccc aagactaagt gaaaggaggt acggggaaa     420 gaggattgtt caatggganat ggggtttaac aacaaaaaat tgttcccaat nncaaggcta   480
atgagctaag cnaaaaattn gagtttaaan ggaatccctt gcaangcaac acaana        536
```

<210> SEQ ID NO 8
<211> LENGTH: 130
<212> TYPE: PRT
<213> ORGANISM: Glycine max
<220> FEATURE:
<221> NAME/KEY: UNSURE
<222> LOCATION: (109)

<400> SEQUENCE: 8

```
Ile Phe Pro Pro Asp Gly Tyr Leu Lys Ala Val Arg Asp Leu Cys Ser
  1               5                  10                  15

Lys Tyr Asn Val Leu Met Ile Ala Asp Glu Ile Gln Thr Gly Leu Ala
             20                  25                  30

Arg Thr Gly Lys Met Leu Ala Cys Glu Trp Glu Glu Val Arg Pro Asp
         35                  40                  45

Val Leu Ile Leu Gly Lys Ala Leu Gly Gly Gly Val Ile Pro Val Ser
     50                  55                  60

Ala Val Leu Ala Asp Lys Asp Val Met Leu Cys Ile Gln Pro Gly Gln
 65                  70                  75                  80

His Gly Ser Thr Phe Gly Gly Asn Pro Met Ala Ser Ala Val Ala Ile
                 85                  90                  95

Ala Ser Leu Glu Val Ile Lys Asn Glu Arg Leu Val Xaa Arg Ser Ala
            100                 105                 110

Gln Met Gly Glu Glu Leu Thr Gly Gln Leu Leu Lys Ile Gln Gln Gln
        115                 120                 125

Tyr Pro
    130
```

<210> SEQ ID NO 9
<211> LENGTH: 994
<212> TYPE: DNA
<213> ORGANISM: Triticum aestivum
<220> FEATURE:
<221> NAME/KEY: unsure
<222> LOCATION: (458)
<220> FEATURE:
<221> NAME/KEY: unsure
<222> LOCATION: (719)
<220> FEATURE:
<221> NAME/KEY: unsure
<222> LOCATION: (817)
<220> FEATURE:
<221> NAME/KEY: unsure
<222> LOCATION: (843)
<220> FEATURE:
<221> NAME/KEY: unsure
<222> LOCATION: (860)
<220> FEATURE:
<221> NAME/KEY: unsure
<222> LOCATION: (876)
<220> FEATURE:

```
<221> NAME/KEY: unsure
<222> LOCATION: (887)
<220> FEATURE:
<221> NAME/KEY: unsure
<222> LOCATION: (899)
<220> FEATURE:
<221> NAME/KEY: unsure
<222> LOCATION: (912)
<220> FEATURE:
<221> NAME/KEY: unsure
<222> LOCATION: (936)
<220> FEATURE:
<221> NAME/KEY: unsure
<222> LOCATION: (969)

<400> SEQUENCE: 9
gcacgaggcc gaaggagtgg aaacggctat taaattggca agaaaatggg gttatgaaaa      60
gaagaatata ccaaagaacg aggctttgat tgtctcttgc tgtggatgtt ccatggtcg     120
gacgttgggg gtcatttcta tgagctgtga caatgatgca actcgtggtt ttggtccttt    180
ggttcctggt catcttaaag ttgattttgg agacattgat gggttggaga aatctttaa    240
agagcatggg gatcgtatat gcggtttttt gtttgaacca atccaaggag aagctggggt    300
aataatccca ccagatggtt atttgaaagc tgtcagagat ttgtgctcta ggcacaacat    360
tctgatgatt gatgatgaga tccaaacagg catacctcga actggcaaaa tgttggcatg    420
cgattgggaa ggtgtacgac ctgatatggt gattctangc aaggcacttg gtgctgagta    480
ttccgtcagt gcagttctcg ccgataagga tatcatgctg tgtatcaagc caggagaaca    540
tggaagtaca tttggtggaa acccattggc aagtgctgtg gcagtcgcat ctctgaaagt    600
ggtcaaggat gaaggtcttg ttgaaagagc cgcggagtta ggtcaggagt tcagagacca    660
gttacaaaag gttcaacaga agtttcctca tattatcagg gaaatacgtg ggagaggtnt    720
gcttaatgca gtaagaccta tgcagcaaag tctataccct gcttctgcat atgacatttg    780
catcaagcta aaggagaaga ggcattctgg gcaaaaccca ccatgacacc attaccggtt    840
aanccctccc tttcaatcan ttctgaggac tcgcanaaca tcaaagnact caacgattnc    900
ccaacatgac tnccgcattt cagagcaatt aagaacaga tccggaggaa acacaatct     960
cgaaagtcng ccggattata aagggggacct tcac                              994

<210> SEQ ID NO 10
<211> LENGTH: 266
<212> TYPE: PRT
<213> ORGANISM: Triticum aestivum
<220> FEATURE:
<221> NAME/KEY: UNSURE
<222> LOCATION: (153)
<220> FEATURE:
<221> NAME/KEY: UNSURE
<222> LOCATION: (240)

<400> SEQUENCE: 10

His Glu Ala Glu Gly Val Glu Thr Ala Ile Lys Leu Ala Arg Lys Trp
 1               5                  10                  15

Gly Tyr Glu Lys Lys Asn Ile Pro Lys Asn Glu Ala Leu Ile Val Ser
            20                  25                  30

Cys Cys Gly Cys Phe His Gly Arg Thr Leu Gly Val Ile Ser Met Ser
        35                  40                  45

Cys Asp Asn Asp Ala Thr Arg Gly Phe Gly Pro Leu Val Pro Gly His
    50                  55                  60

Leu Lys Val Asp Phe Gly Asp Ile Asp Gly Leu Glu Lys Ile Phe Lys
65                  70                  75                  80
```

```
Glu His Gly Asp Arg Ile Cys Gly Phe Leu Phe Glu Pro Ile Gln Gly
             85                  90                  95

Glu Ala Gly Val Ile Pro Pro Asp Gly Tyr Leu Lys Ala Val Arg
        100                 105                 110

Asp Leu Cys Ser Arg His Asn Ile Leu Met Ile Asp Asp Glu Ile Gln
            115                 120                 125

Thr Gly Ile Pro Arg Thr Gly Lys Met Leu Ala Cys Asp Trp Glu Gly
        130                 135                 140

Val Arg Pro Asp Met Val Ile Leu Xaa Lys Ala Leu Gly Ala Glu Tyr
145                 150                 155                 160

Ser Val Ser Ala Val Leu Ala Asp Lys Asp Ile Met Leu Cys Ile Lys
                165                 170                 175

Pro Gly Glu His Gly Ser Thr Phe Gly Gly Asn Pro Leu Ala Ser Ala
                180                 185                 190

Val Ala Val Ala Ser Leu Lys Val Val Lys Asp Glu Gly Leu Val Glu
            195                 200                 205

Arg Ala Ala Glu Leu Gly Gln Glu Phe Arg Asp Gln Leu Gln Lys Val
        210                 215                 220

Gln Gln Lys Phe Pro His Ile Ile Arg Glu Ile Arg Gly Arg Gly Xaa
225                 230                 235                 240

Leu Asn Ala Val Arg Pro Met Gln Gln Ser Leu Tyr Pro Ala Ser Ala
                245                 250                 255

Tyr Asp Ile Cys Ile Lys Leu Lys Glu Lys
                260                 265

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:PCR PRIMER

<400> SEQUENCE: 11
cgatgaatac tggtgctgaa gg                                            22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:PCR PRIMER

<400> SEQUENCE: 12
cacaaatccg atctccaagc tc                                            22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:PCR PRIMER

<400> SEQUENCE: 13
accccagctt caccttggat ag                                            22

<210> SEQ ID NO 14
<211> LENGTH: 23
<212> TYPE: DNA
<213> ORGANISM: Artificial Sequence
<220> FEATURE:
```

-continued

```
<223> OTHER INFORMATION: Description of Artificial Sequence:PCR PRIMER

<400> SEQUENCE: 14
tggatctcat cagcaatcat caa                                              23
```